United States Patent [19]

Roane

[11] Patent Number: 5,145,373
[45] Date of Patent: * Sep. 8, 1992

[54] ENDODONTIC POST

[76] Inventor: James B. Roane, 707 Southwest 24th St., Norman, Okla. 73069

[*] Notice: The portion of the term of this patent subsequent to Jul. 30, 2008 has been disclaimed.

[21] Appl. No.: 701,671

[22] Filed: May 16, 1991

Related U.S. Application Data

[63] Continuation-in-part of Ser. No. 308,046, Feb. 9, 1989, Pat. No. 5,035,620.

[51] Int. Cl.$^5$ .............................. A61C 5/08
[52] U.S. Cl. .................... 433/221; 433/224
[58] Field of Search ............... 433/220, 221, 224, 225, 433/102, 165, 166

[56] References Cited

U.S. PATENT DOCUMENTS

| | | | |
|---|---|---|---|
| D. 273,984 | 5/1984 | Vlock | D24/10 |
| 430,522 | 6/1890 | Genese | |
| 758,750 | 5/1904 | Haldeman | |
| 1,119,407 | 12/1914 | Davis | |
| 1,285,758 | 11/1918 | McMahon et al. | 433/221 |
| 3,590,486 | 7/1971 | Brenner et al. | 32/15 |
| 3,675,328 | 7/1972 | Weissman | 32/15 |
| 3,675,329 | 7/1972 | Weissman | 32/15 |
| 3,728,794 | 4/1973 | Edelman | 32/15 |
| 3,740,851 | 6/1973 | Weissman | 32/15 |
| 3,855,702 | 12/1974 | Malmin | 433/224 |
| 3,861,043 | 1/1975 | Lieb et al. | 32/15 |
| 3,874,081 | 4/1975 | Franklin et al. | 32/15 |
| 3,894,339 | 7/1975 | Manzi | 433/166 |
| 4,060,896 | 12/1977 | Wahnish | 32/10 A |
| 4,229,169 | 10/1980 | Smith et al. | 433/174 |
| 4,234,309 | 11/1980 | Sellers | 433/225 |
| 4,259,076 | 3/1981 | Yanney | 433/225 |
| 4,268,253 | 5/1981 | Gross et al. | 433/221 |
| 4,276,027 | 6/1981 | Lustig | 433/225 |
| 4,290,756 | 9/1981 | Sellers | 433/225 |

(List continued on next page.)

FOREIGN PATENT DOCUMENTS

| | | | |
|---|---|---|---|
| 548228 | 4/1932 | Fed. Rep. of Germany | 433/220 |
| 579504 | 6/1933 | Fed. Rep. of Germany | 433/220 |
| 3427172 | 1/1986 | Fed. Rep. of Germany | 433/225 |
| 3905126 | 9/1989 | Fed. Rep. of Germany | 433/225 |
| 361315 | 11/1931 | United Kingdom | 433/165 |

OTHER PUBLICATIONS

CDA Journal, "Preparing Severely Damaged Teeth", by Shillingburg, Jr., et al., Mar., 1983, 85-91.
Exhibit A—photograph of Model C-1 post made by the Parkall Company.
Exhibit B—photograph of a post manufactured by Dentatus.
Exhibit C—photograph of BCH post.
Exhibit D—photograph of a post made by Parapost.
Exhibit E—photograph of another post manufactured by Parapost.
Exhibit F—photograph of several posts manufactured by Kurer.
Exhibit G—photograph of a post constructed generally like that shown in U.S. Pat. No. 4,479,783 to Weissman at FIGS. 2 and 3.
Exhibit H—photograph of a post having an external spiral thread along with a vertical vent groove.

Primary Examiner—Robert P. Swiatek
Assistant Examiner—Nicholas D. Lucchesi
Attorney, Agent, or Firm—Laney, Dougherty, Hessin & Beavers

[57] ABSTRACT

An endodontic post has at least two graduated stages of decreasing diameter with generally cylindrical outer surfaces. The graduations allow the post to diminish in size as it passes into a prepared post space which can be complementarily graduated. The staged post may also include a single groove having a pitch angle in a range of from about 35° to about 55° disposed in the cylindrical outer surfaces thereof.

A graduated endodontic drill has at least two cutting stages of decreasing diameter for cutting through tooth material to make a prepared post space.

15 Claims, 4 Drawing Sheets

U.S. PATENT DOCUMENTS

| | | | |
|---|---|---|---|
| 4,349,335 | 9/1982 | Weissman | 433/225 |
| 4,365,958 | 12/1982 | Vlock | 433/225 |
| 4,397,634 | 8/1983 | Biggs | 433/225 |
| 4,431,416 | 2/1984 | Niznick | 433/174 |
| 4,466,795 | 8/1984 | Plischka | 433/166 |
| 4,468,200 | 8/1984 | Munch | 433/174 |
| 4,479,783 | 10/1984 | Weissman | 433/221 |
| 4,490,116 | 12/1984 | Deutsch et al. | 433/215 |
| 4,500,296 | 2/1985 | Friedman | 433/225 |
| 4,579,532 | 4/1986 | Lustig | 433/225 |
| 4,600,392 | 7/1986 | Weissman | 433/225 |
| 4,655,711 | 4/1987 | Weissman | 433/225 |
| 4,708,655 | 11/1987 | Weissman | 433/225 |
| 4,713,004 | 12/1987 | Linkow et al. | 433/174 |
| 4,713,006 | 12/1987 | Hakamatsuka et al. | 433/201.1 |
| 4,729,736 | 3/1988 | Weissman | 433/221 |
| 4,738,616 | 4/1988 | Reynaud | 433/220 |
| 4,758,160 | 7/1988 | Ismail | 433/173 |
| 4,767,332 | 8/1988 | Weissman | 433/225 |
| 4,904,185 | 2/1990 | McSpadden | 433/102 X |
| 4,932,870 | 6/1990 | Miller | 433/225 X |
| 4,949,479 | 4/1976 | Malmin | 433/224 |
| 5,035,620 | 7/1991 | Roane | 433/221 |

ENDODONTIC POST

This application is a continuation-in-part of co-pending application U.S. Ser. No. 07/308,046 filed Feb. 9, 1989 now U.S. Pat. No. 5,035,620, by James B. Roane entitled "Endodontic Post With Spiral Groove".

1. Field of the Invention

This invention relates to endodontic post and drill constructions for use in fabricating a tooth restoration for a portion of an injured tooth.

2. Description of the Prior Art

When repairing severely damaged teeth, a dental post or endodontic post is often utilized to help anchor a tooth restoration such as an artificial crown to a remaining root portion of a tooth. For example, the crown may be broken from a tooth by a traumatic injury or may have substantial portions thereof removed due to removal of decayed areas, thus leaving the root or roots of the tooth along with a relatively short stub of the original crown extending above the patient's gum area.

When the damage to the tooth is such that it is necessary to remove the pulp material from the root canals, it is common to use an endodontic post to help anchor the artificial crown to the remaining original tooth structure. An endodontic post is a cylindrical pin which is cemented into the endodontically prepared root canal and extends above the surface of the remaining natural tooth to serve as an anchor for the artificial crown restoration which is attached to the remaining natural tooth.

In multi-canaled teeth such as molars, there will typically be two such posts, one placed in each of two separate canals. In single-canaled teeth, typically a single cylindrical post will be placed in the canal.

A general description of these prior art procedures utilizing endodontic posts, both in multi-canaled and single-canaled teeth is provided in "Preparing Severely Damaged Teeth", March, 1983, *CDA Journal*, pages 85-91 by Shillingburg, Jr., et al.

The posts utilized for such tooth restorations are typically cylindrical, often having grooves, threads or flutes formed in the post for aiding in cementing the post in place and/or venting cement from the root canal as the post is placed in the canal.

One typical prior art construction for such a post is that shown in FIG. 1 of U.S. Pat. No. 4,479,783 to Weissman. The post shown in FIG. 1 of Weissman has a spiral groove or thread 18 cut therein at a very large pitch angle to the longitudinal axis of the post. The pitch of the spiral groove is so great that it cannot effectively function as a vent. A longitudinally extending vent 24 is provided.

FIGS. 2 and 3 of U.S. Pat. No. 4,479,783 to Weissman disclose another helically fluted dental post which has a plurality of grooves placed at a very shallow (approximately 7°) pitch angle. The shallow spiral flutes in FIGS. 2 and 3 of the Weissman '783 patent function as vents, and additionally help retain the post in place once it is cemented within a prepared root canal.

Other disclosures similar to that of FIGS. 2 and 3 of Weissman U.S. Pat. No. 4,479,783 are found in U.S. Pat. Nos. 4,729,736; 4,708,655; and 4,600,392, all also to Weissman.

U.S. Pat. No. 4,268,253 to Gross et al., discloses an endodontic post having a generally polygonal cross section which has been twisted to form a plurality of side-by-side vent grooves. The outer surface of the Gross et al. post is substantially completely covered with grooves and there is no significant non-grooved portion.

U.S. Pat. No. 4,276,027 to Lustig and U.S. Pat. No. 4,490,116 to Deutsch et al., both show endodontic posts having straight longitudinal vent grooves. The Deutsch et al. '116 patent further discloses an increased diameter upper stage.

U.S. Pat. No. 4,579,532 to Lustig also discloses a multi-stage endodontic pin.

U.S. Pat. No. 430,522 to Genese shows a cylindrical endodontic post having a continuous conical taper. U.S. Pat. Nos. 4,234,309 and 4,290,756 to Sellers show cylindrical, continuously tapered endodontic posts further provided with spiral screw threads.

SUMMARY OF THE INVENTION

An endodontic post construction of the present invention has an elongated cylindrical outer surface with one and only one spiral groove defined in the outer surface. The groove has a pitch angle in the range of from about 35° to about 55° to the longitudinal axis of the post. This groove provides three different functions. First, it functions as a vent means for venting air and/or cement as the post is placed in an endodontically prepared root canal. Second, the groove serves as a retention means for aiding retention of the post when it is cemented in the prepared root canal. Third, the groove provides a thread means which aids in removal of the post in the event that removal is necessary.

The groove is preferably semi-circular in cross section having a radius in the range from about 5% to about 30% of a diameter of the cylindrical outer surfaces. An ungrooved area of the outer cylindrical surface of the post is substantially greater than a grooved area of the outer cylindrical surfaces.

Another aspect of the invention is an elongated endodontic post with at least two graduated stages of decreasing diameter each of which has generally cylindrical outer surfaces extending substantially over its entire length. The stages can have large, intermediate and small diameters. The decreasing diameters allow the post to diminish in size as it passes into a prepared post space which can be complementarily graduated in shape.

A further aspect of the invention is an endodontic post construction having at least two graduated stages of decreasing diameter with generally cylindrical outer surfaces substantially over the entire length of each stage wherein one and only one spiral groove is defined. This post construction combines the graduated stages and single spiral groove features described above to provide a post which decreases in diameter as it passes into a complementarily graduated prepared post space and where the single spiral groove functions as a vent means, retention means and thread means. Since the major part of the post cylindrical outer surface is ungrooved, the post remains relatively strong.

The spirally grooved endodontic posts of the present invention provide significant advantages over the various other prior art post designs, in that a single groove functions as a vent, as a retention means, and as a thread means, while still providing a cylindrical post the majority of which is not interrupted by grooves thus providing a relatively strong post.

Graduated diameter stages allow graduated posts to diminish in size as they pass into prepared post spaces. The cylindrical graduated stages of the post have parallel sides which allow the post to taper, while retaining the superior extraction resistance provided by parallel post and post space walls by comparison to the extraction resistance of continuously tapered posts whose sides are not parallel to the post space walls at every point.

Complementarily graduated post spaces having at least two stages of decreasing diameter and a generally cylindrical inner surface over substantially the entire length of the prepared post space can be provided as part of a tooth restoration.

The graduated post space can be prepared precisely in a single step process using a drill including a bit having at least two graduated cutting stages of decreasing diameter and a generally cylindrical outer surface complementarily graduated to a graduated post. The prepared post space has a slightly larger diameter than the post.

Numerous objects, features and advantages of the present invention will be readily apparent to those skilled in the art upon a reading of the following disclosure when taken in conjunction with the accompanying drawings.

DETAILED DESCRIPTION OF THE PREFERRED EMBODIMENTS

Figures 1, 2, 4, 6:
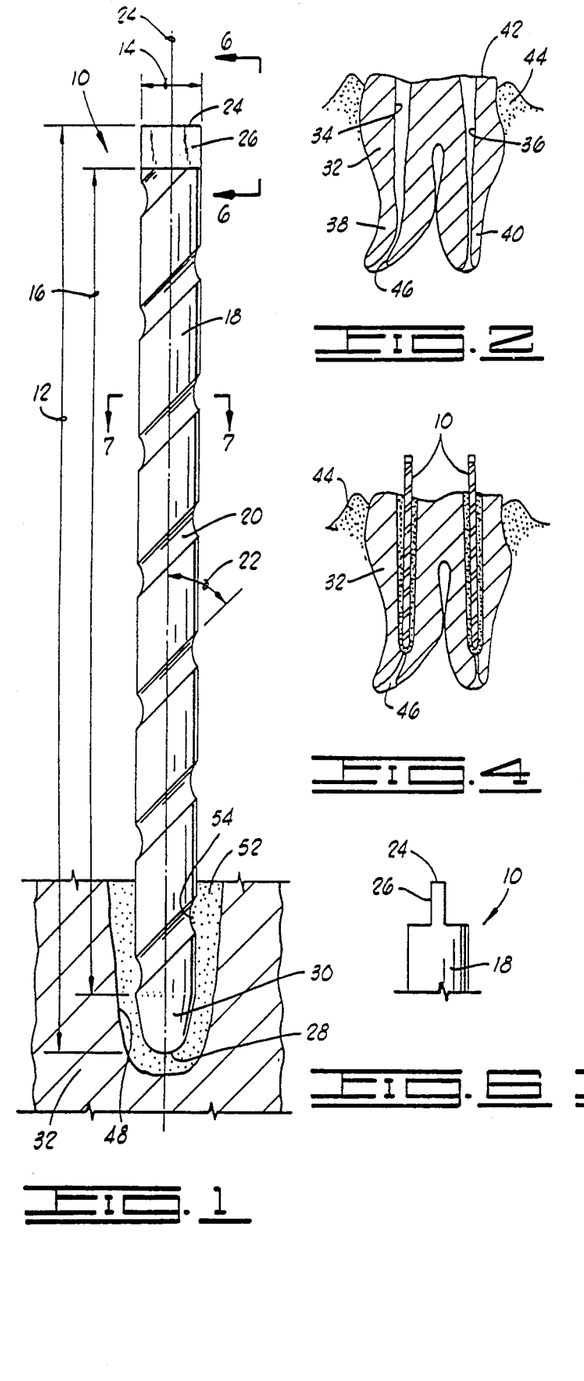
FIG. 1 is an elevation view of a spirally grooved endodontic post of the present invention. A lower portion of a root canal is shown having the lower tip of the post received therein.
FIG. 2 is an elevation sectioned view of a multi-canaled tooth. The upper portion of the tooth has been broken off or removed.
FIG. 4 illustrates the tooth of FIG. 3 after spirally grooved endodontic posts have been cemented in place within the prepared canals.
FIG. 6 is a partial elevation view of the upper end of the post of FIG. 1 taken along line 6—6 of FIG. 1.

In FIG. 1, the endodontic post of the present invention is shown and generally designated by the numeral 10. The post 10 generally has an elongated cylindrical shape, and has a length 12 and a diameter 14.

A major portion 16 of the length 12 is cylindrical in shape, having a cylindrical outer surface 18. A spiral groove 20 is defined in the cylindrical outer surface 18. There is one and only one spiral groove 20 defined in the cylindrical outer surface 18. The groove 20 is set at a pitch angle 22 in a range of from about 35° to about 55°. Preferably, the pitch angle 22 is approximately 45°.

The groove 20 preferably has a smooth curvilinear cross section, and preferably is semi-circular in cross section. The semi-circular cross-section groove 20 preferably has a radius, and thus a depth within post 10, from about 5% to about 30% of the diameter 14 of the outer cylindrical surface 18 of the post 10. Preferably, the groove 20 has a depth in a range of from about 15% to about 20% of the diameter 14.

It will be appreciated by those skilled in the art that endodontic posts such as the post 10 are typically provided in several different diameters so that a suitable post can be selected to be relatively closely received within a prepared root canal of a human tooth. Typical diameters in which posts such as the post 10 are provided are 1.0 mm., 1.2 mm., 1.4 mm., and 1.6 mm. These posts typically have a length of less than 20 mm.

The post 10 illustrated in FIG. has been drawn approximately to scale to represent a 1.6 mm. diameter post, 20 mm. in length, having a groove of 0.3 mm. radius set at a pitch angle of 45°. Thus, the groove 22 spirals around the post 10 approximately six times.

Figure 7:
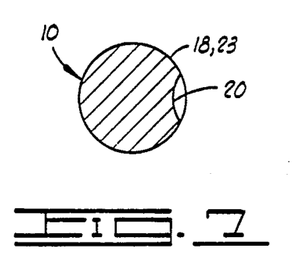
FIG. 7 is a cross-sectional view of the post of FIG. 1, taken along line 7—7.

As is apparent in FIG. 1, with such a construction, an ungrooved area of the outer cylindrical surface 18 is substantially greater than a grooved area of the outer cylindrical surface 18. As is apparent in FIG. 7, any cross-section of the cylindrical portion 16 of post 10 comprises a circular periphery 23 interrupted at one location by groove 20. Since groove 20 is smooth in cross-section, there are no significant points of stress concentration created.

This substantial ungrooved area of outer cylindrical surface 18 provides an important function in addition to the fact that it provides a strong uninterrupted cross-sectional area. It also resists rotational motion of the tooth restoration 56 relative to the post 10. This is particularly true as compared to the relative performance of a post like that of U.S. Pat. No. 4,268,253 to Gross et al. which has its entire outer surface grooved. When the tooth restoration 56 is subjected to chewing forces, those forces both push down on tooth restoration 56 and twist tooth restoration 56. When twisting forces are applied to a restoration mounted on a post like that of the Gross et al. '253 patent, the restoration tends to climb the incline of the external flutes of the post as it twists. This causes a repeated lifting force on the restoration and on the post relative to the cement which tends to break the bonds between the post and both the restoration and the cement. With the post 10 of the present invention, however, the ungrooved cylindrical surface 18 resists these twisting forces without creating a lifting force and thus provides a more secure bond between the post and both the restoration and the cement.

Post 10 has an axially outer end 24 on which is defined a wrench flat 26 which may be generally referred to as an engagement means 26 for engaging a tool, such as a wrench, for rotating the post 10 to thread the post 10 out of a prepared root canal.

An axially inner end 28 of the post 10 has a tapered and rounded tip means 30 defined thereon for minimizing stress concentrations at areas of engagement of the inner end 28 of post 10 with a tooth.

In FIG. 2, a human tooth 32 is shown. The tooth 32 illustrated is a molar tooth having two root canals 34 and 36 extending down into root portions 38 and 40 of the tooth.

An irregular upper surface 42 is shown where the tooth 32 has been broken off or cut away. Gum tissue 44 is illustrated adjacent the broken upper surface 42 of the tooth.

The root canal 34 extends downward from the upper surface 42 to an apical foramen or opening 46 in the lower end of the root 38. The root canal 36 is similarly formed.

Figure 3:
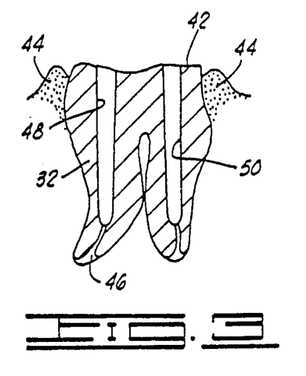
FIG. 3 is a view of the tooth of FIG. 2 after the root canals have been endodontically prepared to form endodontic post spaces for receiving a post construction.

Prior to placement of a tooth restoration or artificial crown on the tooth 32, the root canals 34 and 36 will typically be endodontically prepared in a manner well known to those skilled in the art through the use of endodontic files to enlarge the root canals 34 and 36 removing the pulp material therefrom and providing enlarged prepared root canals a portion of which can be referred to as endodontic post spaces 48 and 50 as illustrated in FIG. 3.

In FIG. 4, two of the posts 10 have been inserted in and cemented in place within the prepared post spaces 48 and 50.

As will be appreciated by those skilled in the art, cement may be placed within the post spaces 48 and 50 prior to insertion of the posts 10, or the posts 10 may be coated with cement prior to being inserted within the post spaces 48 and 50. Also, cement may be placed within the post spaces 48 and 50 and also coated on the posts 10 prior to insertion In any event, the posts 10 are inserted within the post spaces 48 and 50 and cemented in place therein.

It is significant to note that the posts 10 are generally not threaded into the post spaces 48 and 50. As best illustrated in the lower portion of FIG. cement 52 generally surrounds the post 10, and the post 10 is not actually tightly wedged or threaded into the post space 48. It is the cement 52 which binds the post 10 to the tooth 32, rather than a mechanical engagement of the post 10 with the tooth material 32 as is the case with many prior art threaded posts.

After the cement 52 has set, however, a spiral ridge 54 of cement is formed within the groove 20.

Figure 5:
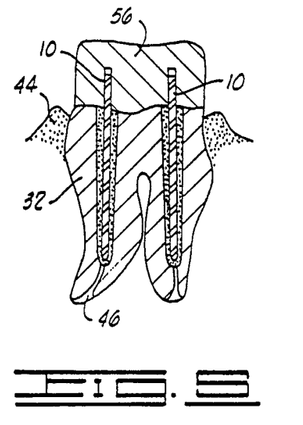
FIG. 5 illustrates the tooth of FIG. 4 after a tooth restoration has been mounted on the tooth and anchored by the spirally grooved endodontic post construction.

It is preferred that points of high stress concentration engagement of the post 10 with the post space 48 be avoided. It will be appreciated when one considers the relatively large forces which are applied to the tooth restoration 56 during the chewing of food and the like, that those forces are transmitted to a significant extent downward through the post 10 to the tooth structure 32. Sharp points of engagement between the post 10 and the tooth structure 32, particularly at the inner end 28 thereof can lead to fracturing of the tooth root.

By forming the inner end 28 of post 10 as a smooth tapered rounded tip 30, such stress concentrations are minimized.

The groove 20 of post construction 10 provides three separate important functions.

First, the groove 20 functions as a vent to vent cement and/or air from the post space 48 as the post 10 is inserted downward into the post space 48. This is particularly important when the post space 48 is filled with cement prior to insertion of the post 10.

A second function provided by the spiral groove 20 is that it aids in retention of the post 10 in place within the post space 48 by increasing the area of contact of the post 10 with the cement 52.

Finally, in the unlikely but possible event that it is necessary to remove the post 10 after the cement 52 has set, the post 10 can be readily removed by rotating it in a counterclockwise direction thus unthreading the groove 20 from the ridge 54 of cement.

It is because of this function of unthreading the post 10 to remove it from the tooth 32 that the engagement means 26 is provided on the outer end 24 of post 10. As previously noted, the post 10 is not generally threaded into place within the post space 48 but may simply be longitudinally inserted into the post space 48. It is, however, threaded out of the post space 48 after the cement 52 has set.

A curvilinear cross-section shape and particularly the semicircular cross-section shape previously described for groove 20 is preferred as compared to a square or triangular cross-section groove as it eliminates points of stress concentration within the post 10. This combined with the fact that only a single groove interrupts any cross section of the post 10, reduces the possibility of breakage of the post 10 when subjected to chewing forces.

Figure 8:
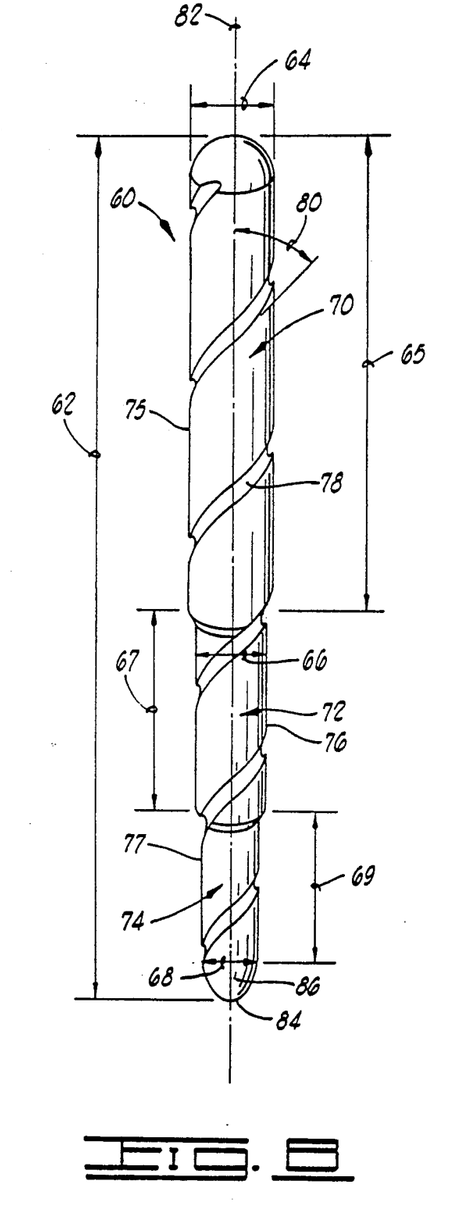
FIG. 8 is an elevation view of a graduated diameter, spirally grooved endodontic post of the present invention.

FIG. 8 shows graduated diameter, spirally grooved endodontic post 60. Post 60 is characterized by overall length 62 and three decreasing diameters, primary diameter 64 extending over length 65, first decreased diameter 66 extending over length 67 and second decreased diameter 68 extending over length 69. Diameters 64, 66 and 68 allow post 60 to diminish in size as it passes into a prepared post space having complementarily graduated stages, which can coincide with natural root taper. While three graduated stages are shown in this preferred embodiment, posts having at least two graduated stages or any number of stages greater than two stages can be fabricated as needed for a particular endodontic post application. The prepared post space can be formed by sequentially drilling each graduation to the required depth with a corresponding diameter drill or can be drilled more precisely in a single step with a complementarily graduated drill of the present invention having at least two stages of decreasing diameter.

Primary stage 70, first decreased diameter stage 72 and second decreased diameter stage 74 are all cylindrical in shape and have cylindrical outer surfaces 75, 76 and 77, respectively. Graduated post 60 can have large, intermediate and small diameter stages where the stages have aspect ratios, which are defined as a stage length divided by a stage diameter, in the range 7.5 to 5.5, 1.5 to 3.5 and 2.5 to 3.5, respectively. These ratios are calculated from stage dimensions for different length posts given in Table I. Use of such parallel-sided graduations allows post 60 to taper while retaining superior resistance to extracting forces as a result of parallel surfaces between post 60 and a prepared post space wall as compared to a continuously graduated post whose surfaces are not everywhere parallel to the prepared post space wall. The graduated post design reduces post diameter as it enters a small region of the tooth root, thus reducing stress exerted thereon.

A spiral groove 78 is defined in cylindrical outer surfaces 75, 76 and 77. There is one and only one spiral groove 78 defined in each cylindrical outer surface 75, 76 and 77. Spiral groove 78 is set at pitch angle 80 to a longitudinal axis 82 of post 60. Pitch angle 80 is in a range of from about 35° to about 5°. Preferably, pitch angle 80 is approximately 45°.

Spiral groove 78 preferably has a smooth curvilinear cross-section, and preferably is semi-circular in cross-section. Semi-circular cross section groove 78 preferably has a radius, and thus a depth within post 60 from about 5% to about 30% of primary diameter 64. Preferably, groove 78 has a depth in a range of from about 15% to about 20% of primary diameter 64. Groove depth is substantially constant over all post graduations and may be slightly deeper at points where a transition occurs between graduated stages.

Figure 12:
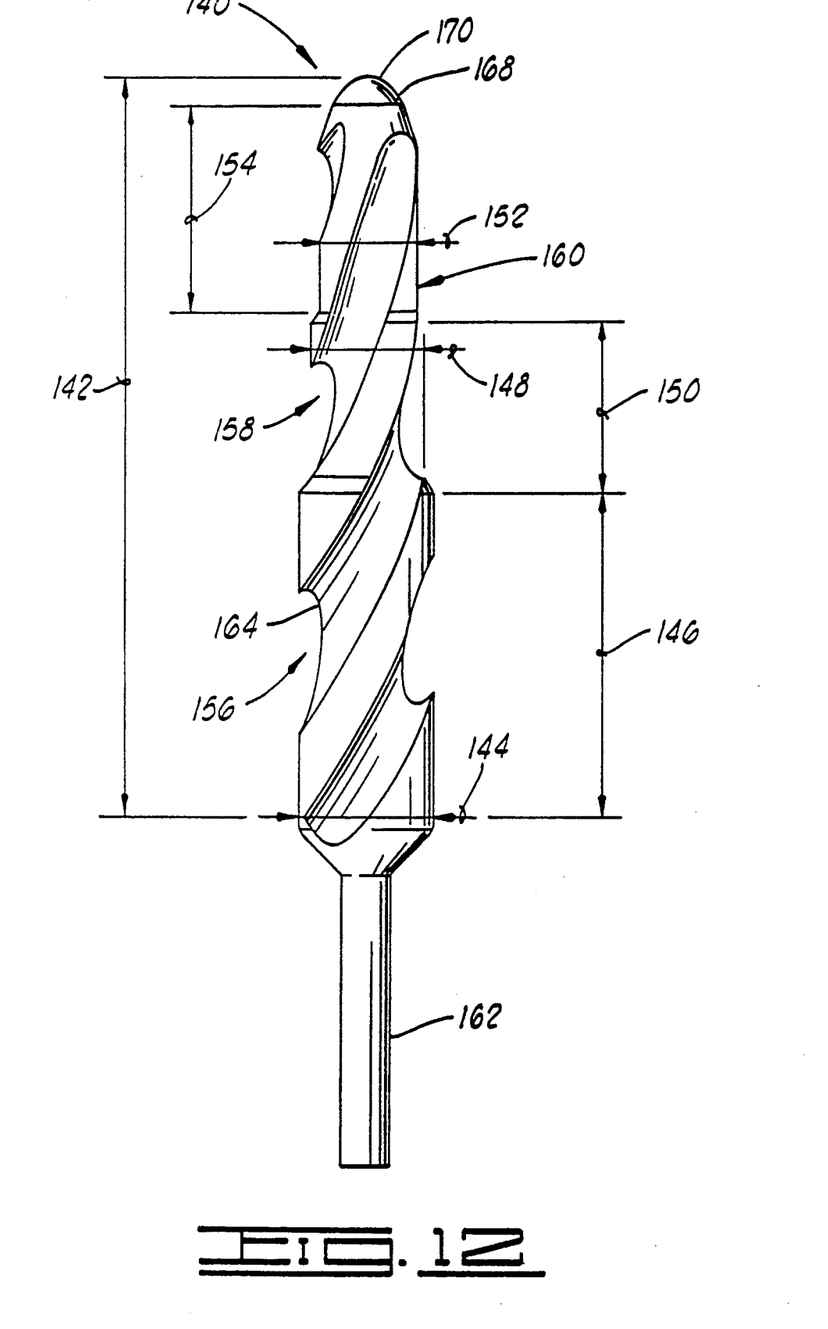
FIG. 12 is an elevation view of a graduated diameter endodontic drill of the present invention.

Post 60 can be provided in several different diameters to provide a post suitably dimensioned to be closely received within a prepared root canal. Typical post primary diameters 64 are 0.6 mm, 0.8 mm, 1.0 mm and 1.2 mm with overall lengths of respectively 10 mm, 12 mm, 15 mm and 18 mm. Typical graduated post design parameters are given in Table I. The design parameters listed in Table I provide examples of stage dimensions for posts having four different lengths. Post length and stage dimensions can be adjusted to fulfill particular post requirements.

which is greater than or equal to the length of an endodontic post which can be placed in a post space prepared using drill 140. Drill 40 is further provided with three graduated diameters, primary diameter 144 extending over length 146, first graduation diameter 148 extending over length 150 and second graduation diameter 152 extending over length 154. Diameters 144, 148 and 152 allow drill 140 to drill a prepared post space having correspondingly graduated diameters and stages corresponding to those of a graduated endodontic post. Primary graduation 156, first graduation 158 and second graduation 160 are all cylindrical in shape. Endodontic drill 140 can have large, intermediate and small diameter stages. Endodontic drill 140 can be used to prepare a graduated post space having large, intermediate and small diameter stages complementarily shaped to an endodontic post which can be inserted into the prepared post space.

Endodontic drill 140 has engagement means 162 at one end which connects the drill to another tool such as a right-angled dental hand piece used to advance the drill within tooth material. Drill flutes 164 remove material as the drill advances to prepare a post space. The drill interior end 168 has rounded tip 170 and does not

TABLE I

| | Graduated Post Design Parameters | | | | | | | |
|---|---|---|---|---|---|---|---|---|
| | Diameter | Length | Diameter | Length | Diameter | Length | Diameter | Length |
| Primary Diameter | 1.6 mm | 11 mm | 1.4 mm | 9.0 mm | 1.2 mm | 7.0 mm | 1.0 mm | 6.0 mm |
| First Decreased Diameter | 1.4 mm | 3.5 mm | 1.2 mm | 3.0 mm | 1.0 mm | 2.5 mm | 0.8 mm | 2.0 mm |
| Second Decreased Diameter | 1.2 mm | 3.5 mm | 1.0 mm | 3.0 mm | 0.8 mm | 2.5 mm | 0.6 mm | 2.0 mm |
| Post Length | | 18 mm | | 15 mm | | 12 mm | | 10 mm |

Axially inner end 84 has a tapered and round tip means 86 to minimize stress concentration at areas of engagement of end 84 with a tooth.

Figure 9:
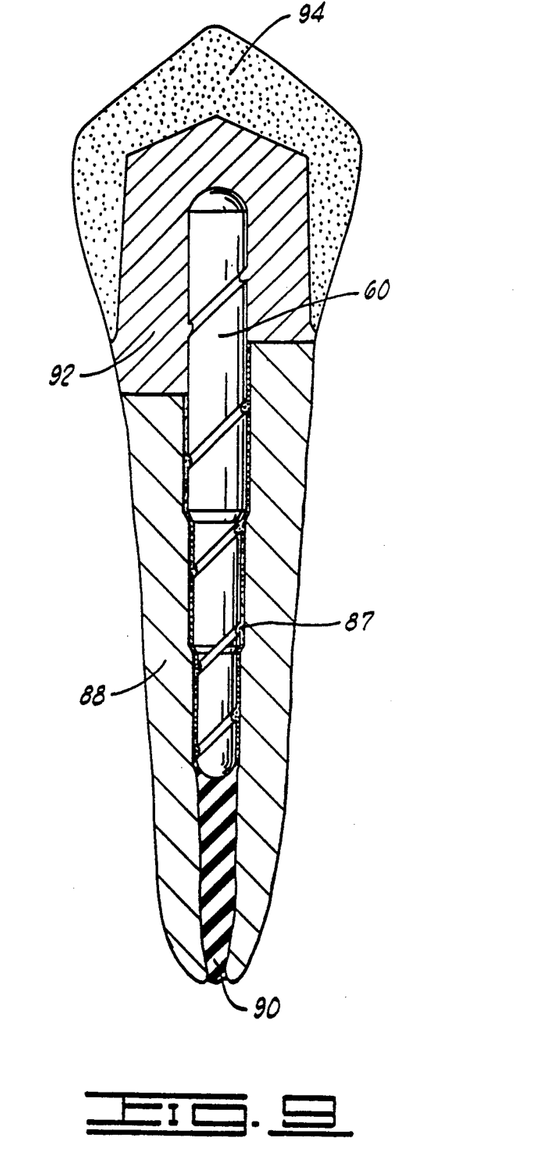
FIG. 9 is an elevation sectioned view of a single-canaled tooth illustrating the graduated diameter, spirally grooved endodontic post in place within a prepared endodontic canal with a tooth restoration anchored by the endodontic post.

FIG. 9 shows graduated, spirally grooved post 60 inserted into prepared, graduated post space 87 in dentine 88 prepared using a complementarily graduated drill shown in FIG. 12. The post space has at least two stages of decreasing diameter and is partially filled with gutta percha or other filler 90. Cement not shown which can be placed in the post space prior to post insertion or coated around the post prior to insertion generally surrounds post 60. Post 60 is neither tightly wedged in the post space nor does it mechanically engage tooth material. Cement bonds post 60 to dentine 88. Amalgam 92 and crown 94 surround post 60. Post 60 can optionally include an engagement means for post removal.

Figure 10:
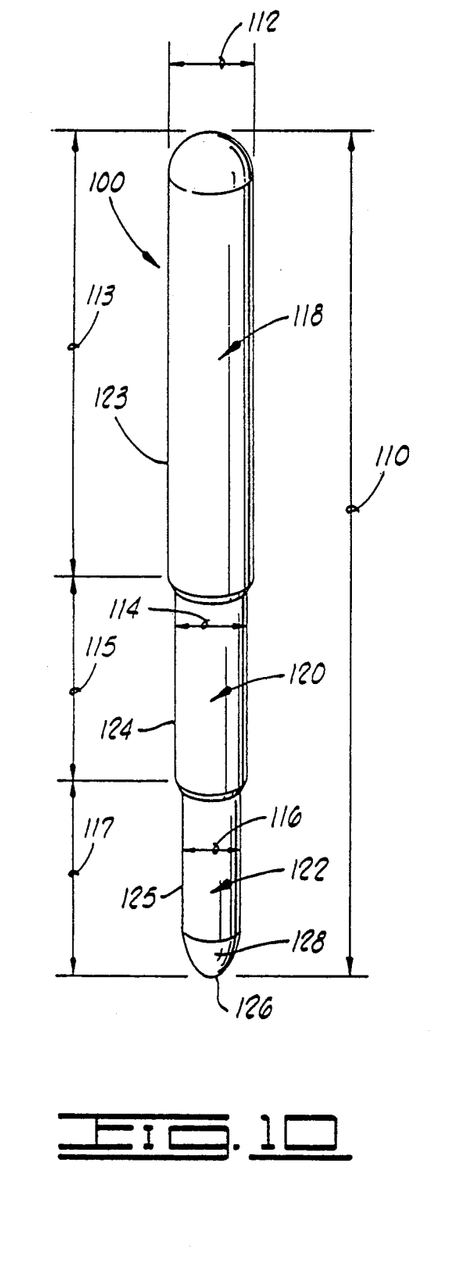
FIG. 10 is an elevation view of a graduated diameter endodontic post of the present invention.

FIG. 10 shows graduated post 100 having overall length and three graduated diameters, primary diameter 112 extending over length 113, first graduation diameter 114 extending over length 115 and second graduation diameter 116 extending over length 117. Each graduation 118, 120 and 122 has a cylindrical outer surface 123, 124 and 125, respectively. Graduated post 100 is the same as post 60 shown in FIG. 8, except that post 100 has smooth, cylindrical outer surfaces 123, 124 and 125, without a spiral groove such as groove 78 of post 60.

Figure 11:
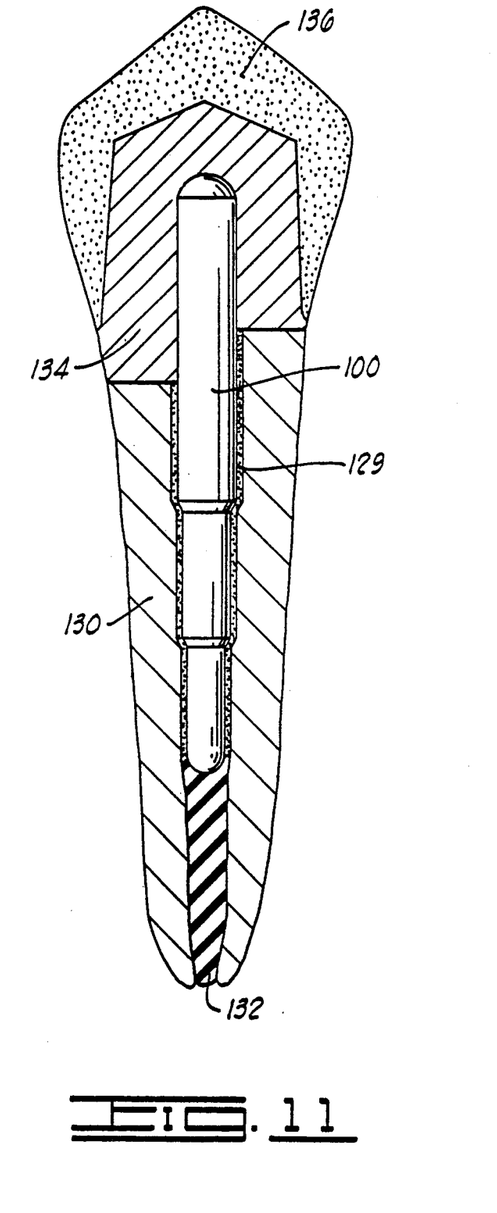
FIG. 11 is an elevation sectioned view of a single canaled tooth, illustrating the graduated diameter endodontic post in place within a prepared endodontic canal with a tooth restoration anchored by the endodontic post.

FIG. 11 shows graduated post 100 inserted into graduated post space 129 prepared into dentine 130 and partially filled with filler 132. Post 100 is inserted into post space 129 using the same method as used for insertion of spirally grooved post 60.

FIG. 12 shows a graduated diameter endodontic drill 140. Drill 140 is characterized by an overall length 142 perform any cutting function.

Use of graduated endodontic drill 140 permits preparation of a graduated prepared post space in a single operation which produces a considerably more precisely shaped prepared post space than could be obtained using a series of conventional drills such as Gates-Glidden drills of varying diameters to sequentially drill multiple stages of a particular diameter to a particular depth.

Thus it is seen that the apparatus and method of the present invention readily achieve the ends and advantages mentioned as well as those inherent therein. While certain preferred embodiments of the invention have been illustrated and disclosed for purposes of the present disclosure, numerous changes in the arrangement and construction of parts and steps may be made by those skilled in the art which changes are encompassed within the scope and spirit of the present invention as defined by the appended claims.

What is claimed is:

1. An endodontic post constructed to be inserted into a prepared post space in a tooth root and cemented in place therein for anchoring a tooth restoration, comprising:

a graduated post having at least two stages of decreasing diameter, said stages having a generally cylindrical outer surface over substantially an entire length of said post;

one and only one spiral groove defined in said cylindrical outer surface of said post, said groove having a pitch angle in a range of from about 35° to about 55° so that said groove provides:

a vent means for venting air and/or cement as said post is placed in said prepared post space;

a retention means for aiding retention of said post when said post is cemented in said prepared post space; and a thread means for threading said post out of said prepared post space in the event of removal of said post; and wherein an ungrooved area of said cylindrical outer surface of said post is substantially greater than a grooved area of said cylindrical outer surface.

2. The endodontic post of claim 1, wherein said pitch angle is approximately 24°.

3. The endodontic post of claim 1, wherein said groove has a smooth curvilinear cross section.

4. The endodontic post of claim 3, wherein said smooth curvilinear cross section is a semi-circular cross section.

5. The endodontic post of claim 4, wherein said semi-circular cross section of said groove has a radius in a range of from about 5% to about 30% of a diameter of said cylindrical outer surface of said post.

6. The endodontic post of claim 1, wherein said groove has a depth in a range of from about 5% to about 30% of a diameter of said cylindrical outer surface of said post.

7. The endodontic post of claim 1, further comprising:

engagement means, defined on an axially outer end of said post for engaging a tool for rotating said post to thread said post out of said prepared post space in the event of removal of said post.

8. The endodontic post of claim 1, further comprising:

a tapered and rounded tip means defined on an axially inner end of said post, for minimizing stress concentrations at areas of engagement of said inner end with said tooth.

9. The endodontic post of claim 1 wherein said stages are a large, intermediate and small diameter stage.

10. The endodontic post of claim 9 wherein said large diameter stage has an aspect ratio in the range 7.5 to 5.5.

11. The endodontic post of claim 9 wherein said intermediate diameter stage has an aspect ratio in the range 1.5 to 3.5.

12. The endodontic post of claim 9 wherein said small diameter stage has an aspect ratio in the range 2.5 to 3.5.

13. The endodontic post of claim 1 wherein said stages of decreasing diameter allow said post to diminish in size as it passes into said prepared post space.

14. A method of anchoring a tooth restoration, said method comprising the steps of:

(a) providing a graduated post having at least two stages of decreasing diameter each of which has a generally straight cylindrical outer surface and one and only one spiral groove defined in said outer surfaces, said groove having a helix angle in a range of from about 35° to about 55°, an ungrooved area of said outer surfaces being substantially greater than a grooved area thereof;

(b) preparing a prepared post space in a tooth, said prepared post space having at least two stages of decreasing diameter complementary to said stages of said post;

(c) inserting said post into said prepared post space and cementing said post therein;

(d) retaining said post in said graduated post space at least partly by means of cement being received in and set up in said groove; and (e) mounting said tooth restoration about said post.

15. The method of claim 14 wherein said preparing step (b) is accomplished by drilling said prepared post space out with a complementarily staged drill.

* * * * *

UNITED STATES PATENT AND TRADEMARK OFFICE
CERTIFICATE OF CORRECTION

PATENT NO. : 5,145,373
DATED : September 8, 1992
INVENTOR(S) : James B. Roane

It is certified that error appears in the above-indentified patent and that said Letters Patent is hereby corrected as shown below:

Column 5, line 40, after "FIG.", insert --1--.

Column 7, line 2, delete "5°" and insert --55°-- therefor.

Column 7, line 53, after "length" insert --110--.

Column 9, line 14, delete "24°" and insert --45°-- therefor.

Signed and Sealed this

Seventh Day of September, 1993

Attest:

BRUCE LEHMAN

*Attesting Officer*       *Commissioner of Patents and Trademarks*